US012714830B2

(12) United States Patent
Illu et al.

(10) Patent No.: US 12,714,830 B2
(45) Date of Patent: Aug. 25, 2026

(54) LIMB CAPTURE DEVICE

(71) Applicant: S-Band LLC, Salt Lake City, UT (US)

(72) Inventors: Thomas Illu, Salt Lake City, UT (US); Seth Illu, Flowery Branch, GA (US); Josh Mayhew, Hooper, UT (US); Mark Wahlen, Bountiful, UT (US)

(73) Assignee: S-Band LLC, Salt Lake City, UT (US)

(*) Notice: Subject to any disclaimer, the term of this patent is extended or adjusted under 35 U.S.C. 154(b) by 313 days.

(21) Appl. No.: 17/962,452

(22) Filed: Oct. 7, 2022

(65) Prior Publication Data

US 2023/0121418 A1 Apr. 20, 2023

Related U.S. Application Data

(60) Provisional application No. 63/360,568, filed on Oct. 15, 2021.

(51) Int. Cl.
*A61M 25/02* (2006.01)
*A61F 5/03* (2006.01)
*A61B 17/00* (2006.01)

(52) U.S. Cl.
CPC ............... *A61M 25/02* (2013.01); *A61F 5/03* (2013.01); *A61B 2017/00951* (2013.01)

(58) Field of Classification Search
CPC .................... A61M 25/02; A61M 5/52; A61M 2025/0213; A61M 25/01–04; A61F 5/37; A61F 5/3715–3792; A61F 5/00; A61F 5/01; A61F 5/04; A61F 5/05; A61F 5/058; A61F 5/05825; A61F 5/05841; A61F 5/05858–05875; A61F 13/10; A61F 13/02; A61F 13/14; A61B 17/3472; A61B 46/00–40; A61G 13/1235; A61G 13/124; A61G 13/12; A61G 13/1205; A61G 13/126; A61G 13/128–1295
USPC .......................................... 604/174; 128/877
See application file for complete search history.

(56) References Cited

U.S. PATENT DOCUMENTS

| | | | | | |
|---|---|---|---|---|---|
| 4,286,588 | A * | 9/1981 | Lovegrove | A61M 5/52 128/877 |
| 4,678,462 | A * | 7/1987 | Vaillancourt | A61M 25/02 128/877 |
| 4,941,480 | A * | 7/1990 | McLean | A61F 5/05841 128/878 |
| 5,358,470 | A * | 10/1994 | Johnson | A61F 5/3746 602/62 |
| 5,785,057 | A | 7/1998 | Fischer | |
| 5,845,643 | A | 12/1998 | Vergano et al. | |
| 6,099,489 | A * | 8/2000 | Herzberg | A61F 13/10 2/45 |
| 8,123,681 | B2 | 2/2012 | Schaeffer | |

(Continued)

FOREIGN PATENT DOCUMENTS

| | | | | |
|---|---|---|---|---|
| DE | 112011100230 T5 * | 10/2012 | | A61F 5/3738 |
| WO | WO-2020028111 A1 * | 2/2020 | | A61B 46/27 |

OTHER PUBLICATIONS

Gazielly, D., Shoulder and arm splint with arm retropulsion control device, Jan. 11, 2011-01-11 (Year: 2011).*

*Primary Examiner* — Alireza Nia
*Assistant Examiner* — Robin Han
(74) *Attorney, Agent, or Firm* — Matthew D. Thayne; Thayne and Davis LLC

(57) ABSTRACT

A limb capture device may include a base with adhesive disposed thereon and a strap for holding a limb to the base to secure the limb.

18 Claims, 6 Drawing Sheets

(56) References Cited

U.S. PATENT DOCUMENTS

| | | | | |
|---|---|---|---|---|
| 8,197,429 | B2 | 6/2012 | Naseem | |
| 11,865,027 | B1 * | 1/2024 | Milton | A61F 5/0111 |
| 2005/0076921 | A1 * | 4/2005 | Rozier | A61M 25/02<br>128/877 |
| 2011/0005525 | A1 * | 1/2011 | Barnes | A61F 5/3723<br>128/845 |
| 2016/0256311 | A1 * | 9/2016 | Lemmon | A61F 5/013 |
| 2017/0020560 | A1 * | 1/2017 | Van Citters | A61B 17/3472 |

* cited by examiner

LIMB CAPTURE DEVICE

REFERENCE

The present application incorporates by references U.S. Provisional Patent Application No. 63/360,568, filed Oct. 15, 2021.

BACKGROUND

Field of Art

The present disclosure relates to a limb capture device. More particularly, the disclosure relates to a device which may be used to secure a person's arm or leg in a particular position when doing so is necessary.

State of Art

There are a variety of medical procedures and other situations where in it is important to maintain a person's limb in a particular position. For example, there are medical procedures in which it is desirable to keep a patient's arm or leg or leg still while performing a procedure. One such procedure is intraosseous (IO) vascular access. When it is difficult to obtain vascular access to the patient to start an IV and the administration of fluids and/or medications is necessary, IO obtains access to the circulatory system by drilling a needle into the medullary cavity of certain bones. The fluids are then pumped into the medullary space from which they are carried into the patient's circulatory system. An IO needle is drilled into the bone and is most often used when the patient is unconscious (vs. an IV inserted into a vein.) The patient, however, could always move responsive to physical stimuli, etc.

Because the size of the medullary cavity impacts the ability to absorb fluid, IO procedures are often conducted on the distal or proximal tibia, the distal femur, the calcaneus, the sternum or the humorous. If an attempt at IO fails, that portion of a limb is typically no longer available for use and another location must be tried. In a situation in which a patient's life is literally on the line, unsuccessful IO placement due to movement of the patient's limb is highly undesirable. While the patient may purposefully or reflexively move a limb, there is also the risk that a member of the medical staff attempting to resuscitate the patient could bump the limb thereby causing an IO placement to fail.

In severe emergency situations, the placing an IO in the humeral head is superior to the proximal tibia, in that medication is able to reach the heart in only 3 seconds. Additionally, the humeral head provides increased flow rate, and better compliance. However, to increase the likelihood of a successful IO placement, it is imperative that the arm is in a fixed position. Otherwise, the IO access point can be easily compromised. Once an IO is displaced, it cannot be placed back on that limb for at least 48 hours. Thus, it is desirable to hold and maintain the patient's arm or other limb in the desired position to keep the IO in place. Thus, it is desirable to provide a limb capture device which will hold the patient's limb so that various procedures may be conducted.

SUMMARY

The following summary of the present disclosure is not intended to describe each illustrated embodiment or every possible implementation of the invention, but rather to give illustrative examples of application of principles of the invention.

One or more of the above-referenced matters may be addressed in a limb capture device which has a base attachable to a surface and a strap for engaging a limb of the person to hold the limb in a desired position. As will be discussed herein, the limb capture device could be used with a patient's arm or a patient's leg depending on the procedure and the position in which the limb is desired to be held.

One or more embodiment of the present disclosure may include a base which an adhesive surface which is selectively covered with a cover. When the cover is removed, the base made be adhesively attached to a desired location.

One or more embodiment may include a strap which is adjustably attached to the base for engaging a limb of a patient. The strap may include an attachment point and an adjustment point so that the strap and be adjusted for the desired size opening between the strap and the base, with an end of the strap folding back on itself and being releasably attachable so that the patient's arm or leg can be securely held during the procedure.

Alternatively, the strap may include an engagement member which allows the strap to be pulled in one direction or the other to change the side of the opening for receiving the patient's limb.

The base and the strap may operate together to secure a person's limb in a desired position. For example, when an IO procedure is being conducted on the humoral head, the cover on the base may be removed and base adhesively attached to the patient's abdomen so that the patient's humorous extends along the torso and the radius and ulna are held across the patients abdomen with the patient's wrist being held between the strap and the base. In such an orientation, the IO procedure and proceed without the risk that the patient's arm will suddenly move and interfere with the IO procedure.

Likewise, if the IO is being placed in the proximal tibia, the limb capture device may be used by placing the patient's leg within the strap and tightening the strap if necessary to hold the patient's leg. The cover of the base may then be removed, and the base be applied to a substrate which will receive and hold the base. For example, during a surgery if an IO procedure is needed, the patient's ankle may be adhesively attached to the operating table. Or the ankle may be attached to the patient's bed. By doing so, the risk that a reflexive move by the patient or a member of the medical team moving the limb by inadvertently bumping it is reduced.

In accordance with the present disclosure, it will be appreciated that the limb capture device is useful in contexts other than placement on an IO. The limb capture device could be beneficial when performing a number of procedures on a child to minimize movement of the child's arm or leg. Likewise, the limb capture device could be used on the limb of a person suffering from Parkinson's disease to minimize movement of the arm or leg while the procedure is proceeding.

The limb capture device could even in use in non-medical situations for a person who has difficultly controlling he or her arm—such as a woman suffering from Parkinson's disease who wants to have her nails done. While the detailed discussion addresses primarily medical uses, it should be remembered that the limb capture device has multiple uses.

These and other aspects of the present disclosure are realized in a toilet freshener/nightlight which includes one or more of the above-referenced features of the present disclosure.

BRIEF DESCRIPTION OF THE DRAWINGS

Various embodiments of the present disclosure are shown and described in reference to the numbered drawings wherein.

Figure 1:
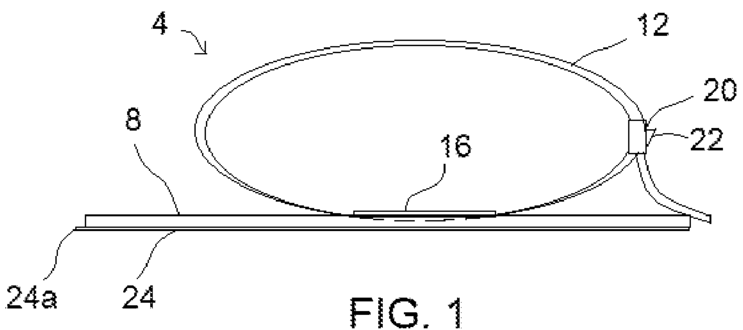
FIG. 1 shows an end view of a limb capture device made in accordance with the principles of the present disclosure.

It will be appreciated that the drawings are illustrative and not limiting of the scope of the invention which is defined by the appended claims. The embodiments shown accomplish various aspects and objects of the invention. It will be appreciated that it is not possible to clearly show each element and aspect of the present disclosure in a single figure, and as such, multiple figures are presented to separately illustrate the various details of different aspects of the invention in greater clarity. Similarly, not all configurations or embodiments described herein or covered by the appended claims will include all the aspects of the present disclosure as discussed above.

DETAILED DESCRIPTION

Various aspects of the invention and accompanying drawings will now be discussed in reference to the numerals provided therein so as to enable one skilled in the art to practice the present invention. The skilled artisan will understand, however, that the apparatus and methods described below can be practiced without employing these specific details, or that they can be used for purposes other than those described herein. Indeed, they can be modified and can be used in conjunction with products and techniques known to those of skill in the art in light of the present disclosure. The drawings and the descriptions thereof are intended to be exemplary of various aspects of examples of the invention and are not intended to narrow the scope of the appended claims. Furthermore, it will be appreciated that the drawings may show aspects of the invention in isolation and the elements in one figure may be used in conjunction with elements shown in other figures, etc.

Reference in the specification to "one embodiment," "one configuration," "an embodiment," or "a configuration" means that a particular feature, structure, or characteristic described in connection with the embodiment may be included in at least one embodiment, etc., but need not be included in any particular embodiment. The appearances of the phrase "in one embodiment" in various places may not necessarily limit the inclusion of a particular element of the invention to a single embodiment, rather the element may be included in one or all embodiments discussed herein.

Furthermore, the described features, structures, or characteristics of embodiments of the present disclosure may be combined in any suitable manner in one or more embodiments. In the following description, numerous specific details may be provided, such as examples of products or manufacturing techniques that may be used, to provide a thorough understanding of embodiments of the invention. One skilled in the relevant art will recognize, however, that embodiments discussed in the disclosure may be practiced without one or more of the specific details, or with other methods, components, materials, and so forth. In other instances, well-known structures, materials, or operations may not be shown or described in detail to avoid obscuring aspects of the invention.

Before the present invention is disclosed and described in detail, it should be understood that the present invention is not limited to any particular structures, process steps, or materials discussed or disclosed herein, but is extended to include equivalents thereof as would be recognized by those of ordinary skill in the relevant art. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of that aspect in the claims.

It should also be noted that, as used in this specification and the appended claims, singular forms such as "a," "an," and "the" may include the plural unless the context clearly dictates otherwise. Thus, for example, reference to "a bracket" may include an embodiment having one or more of such brackets, and reference to "the plate" may include reference to one or more of such plates.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

As used herein, the term "generally" refers to something that has characteristics of a quality without being exactly that quality. For example, a structure said to be generally vertical would be more vertical than horizontal, i.e., would extend greater than 45 degrees from horizontal. Likewise, something said to be generally circular may be rounded like an oval but need not have a consistent diameter in every direction.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range, or the characteristics being described.

Figure 2:
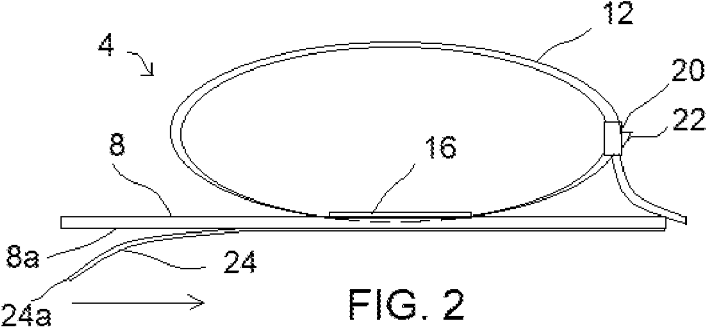
FIG. 2 shows the limb capture device of FIG. 1 with the cover on the base being partially removed.

Turning now to FIG. 1 there is shown an end view of a limb capture device, generally indicated at 4. The limb capture device 4 may include a base 8 and a strap 12. The strap 12 may be attached to the base 8 by a variety of measures includes adhesives, rivets or other mechanical fasteners or, as shown in FIGS. 1-3, by a cross strap 16 which may be attached at both ends to the base with the strap 12 extending between the two.

The strap 12 may be attached to a clasp 20 through which the strap 12 can slide and then a clasp lock 22 may be depressed when the opening defined by the strap 12 is of the desired size. It will be appreciated that there are numerous different attachment members and clasps which can be used to hold to the strap to allow adjustment in size.

Disposed along the bottom of the base 8 may be a removable cover 24. As shown in FIG. 1, the removable cover 24 is covering the bottom of the base with a tab **24*a* extending a short distance from the base. In FIG. 2, the tab 24*a* has been pulled toward the opposite side of the base 8 so as to expose an adhesive underside 8*a* of the base. By continuing to pull the tab 24*a* or other portions of the cover 24 toward the opposing side of the base 8, the entire adhesive underside 8*a*** of the base may be exposed.

Figure 3:
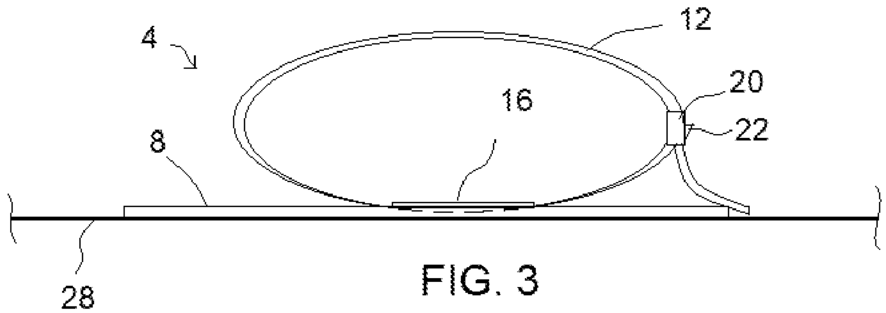
FIG. 3 shows the limb capture device of FIG. 3 with the base attached to a substrate.

In FIG. 3, the adhesive underside of the base 24 has been attached to a substrate 28. The substrate 28 may be a variety of materials depending on the procedure being performed. If an IO procedure is being performed in the humoral head, the substrate 28 may be the skin of the patient's abdomen so that the humorous may extend generally along the side of the patient's torso, while the lower portion of the arm (the radius and ulna) extend generally perpendicular to the length of the torso across the patient's abdomen with the wrist being secured near the other arm.

In the event of a person's leg being held in place, the substrate 28 may be a surgical table, an examination chair or other structure which allows the leg to be held in a desired orientation. Once the patient's limb is securely held by the strap 12 and to the substrate 28 (which can occur in either order), the patient's limb is immobilized and the risk that it is moved in such a way as to interfere with a procedure, or the like is substantially reduced.

Figure 4:
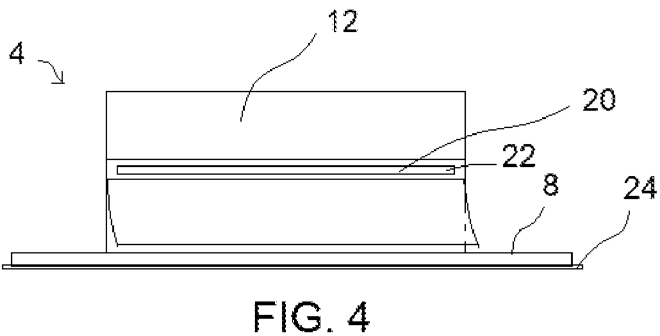
FIG. 4 shows a side view of the limb capture device of FIG. 1.

FIG. 4 shows a side view of the limb capture device 12. While the strap 12 can be of a wide variety of widths, common widths are presently between about 2 and four inches and with an interior diameter between the strap 12 and/or strap and based being adjustable from about 1.5 inches to 5 inches in diameter. In the configuration shown in FIGS. 1-4, the strap 12 may be held to the base 8 only by the cross-strap 16 or may also be mechanically attached by rivets, clamps, etc.

Figure 5:
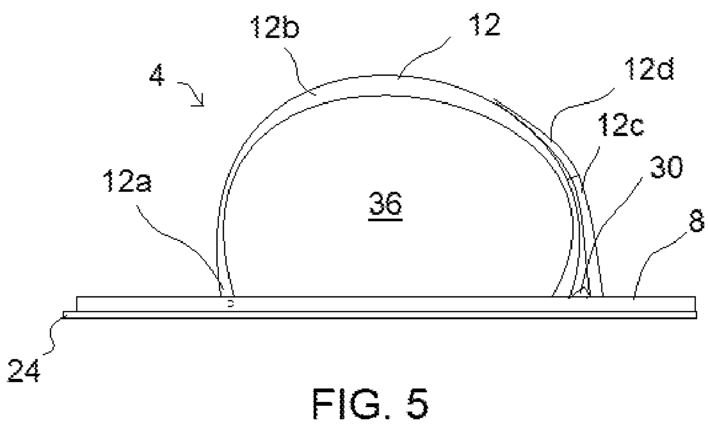
FIG. 5 shows an end view of a limb capture device.
Figure 6:
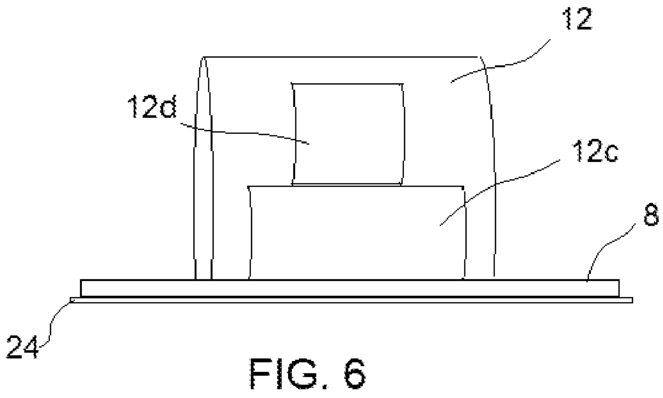
FIG. 6 shows a side view of a limb capture device of FIG. 6.

Turning now to FIGS. 5 and 6, there are shown an end view and a side view, respectively, of a limb capture device, generally indicated at 4. The limb capture device 4 may have a base 8 and a strap 12. The strap may have a first end **12*a* which may be attached to the base 8. The attachment may be formed by adhesive or mechanical means, including glues, ultrasonic welding rivets, staples, clamps and the like. A central portion 12*b* of the strap 12 may extend above the base 8. An end of the central portion 12*b* opposite the first end may slidably engage an anchor 30, so that a second end 12*c* may be pulled out to reduce the length of the central portion 12*b*. The second end 12*c* may double back on the central portion and may include a fastener 12*d* to secure it to central portion 12*b* of the strap 12. The fastener 12*d*** may be hook and loop fastener (e.g., VELCRO) a clamp, buckle, etc.

In use the faster **12*d* may be opened or removed from the central portion 12*b* and the patient's limb inserted into the void 36 under the central portion 12*b* of the strap 12. Once the limb is in place, the second end 12*c* of the strap may be pulled to tighten the strap down on the wrist, ankle or other portion of a limb wished to be held, and the fastener 12*d* fastened to hold secure the limb in the limb capture device. The cover 24 may then be removed from the base 8 and the base adhesively attached to a substrate in a desired location. Alternatively, the base 8 may be attached to the substrate first and then the limb secured in place by the strap 12**.

Figure 7:
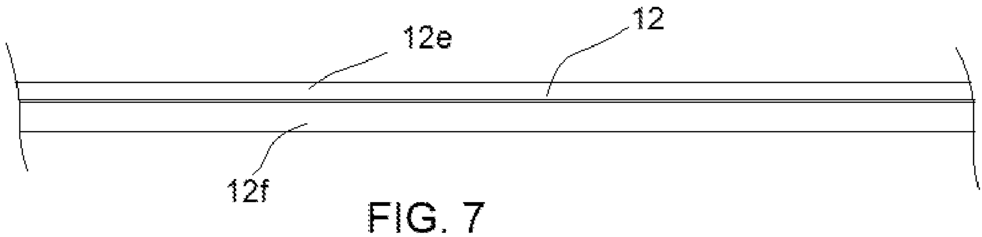
FIG. 7 shows a close-up view of a strap which may be used on a limb capture device.

FIG. 7 shows a close-up view of an embodiment of a strap 12. A strap 12 could be made from an elastic or semi-elastic material similar to an elastic bandage. Alternatively, as shown in FIG. 7, the strap 12 may be made of a first, outer layer **12*e* which is not elastic and an inner layer 12*f*** which is made from a soft material, such as microfiber, cotton or the like, which provides sufficient padding so that the patient's skin is not damaged when the strap is tightened down.

Figure 8:
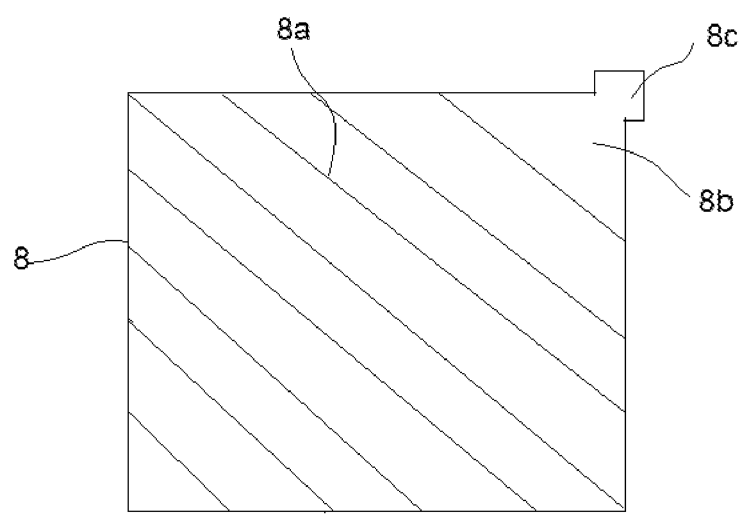
FIG. 8 shows a bottom of a base with the cover removed.
Figure 9:
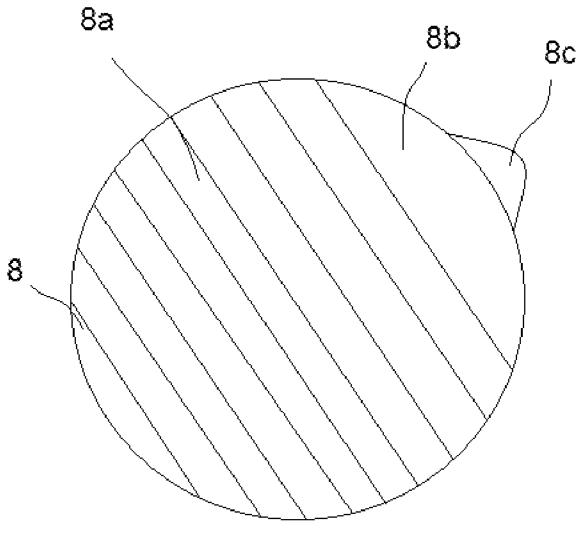
FIG. 9 shows a bottom of a base with the cover removed.

It will be appreciated that numerous modifications may be made. For example, the base 8 could be formed from a single layer or from multiple layers. The underside of the base could be completely covered with adhesive 40 or only portions thereof could be covered so as to leave a corner of the base uncovered as shown at **8*b* in FIG. 8. Additionally, the base 8 may include a tab 8*c*. The tab 8*c* and the uncovered corner 8*b* facilitate peeling the bottom of the base 8 off of the substrate to which it has been attached. The base need not be rectangular. As shown in FIG. 9, the base 8** may be round or any other shape.

Figure 10:
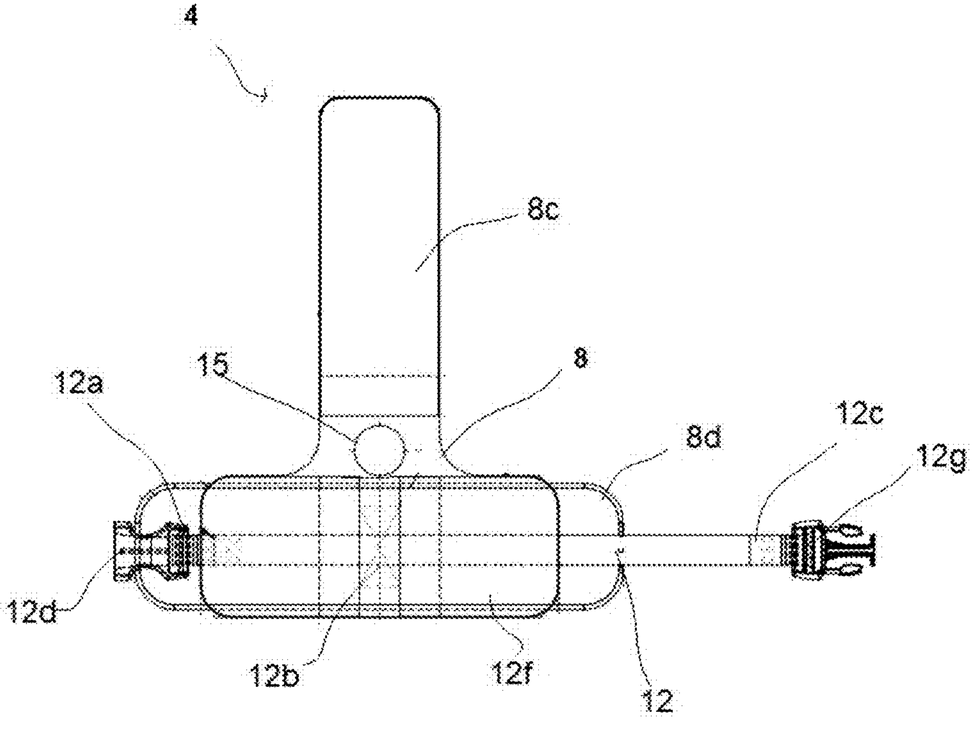
FIG. 10 shows a plan view of a limb capture device.

Turning now to FIG. 10, there is shown a limb capture device, generally indicated at 4. The limb capture device 4 may include a base 8. The base 8 may be made of cloth or some other flexible fabric, or may be rigid depending on the desired use. As shown in FIG. 10, the base 8 may be T-shaped or some other geometry so as to have an arm or tab **8*c* which may have a guide marking 15, such as a hole or other indicator to facilitate alignment of the base 8. The guide marking 15 may be aligned, for example, with the navel of a patient so that the person applying the limb capture device knows that the arm is properly positioned with the wrist of the patient held adjacent the navel to maintain the arm in the desired position for an IO procedure. The tab 8***c* may be, for example, 4 to 10 inches long and 1 to 5 inches wide so as to provide up to 50 square inches of surface area along which the limb capture device 4 may be held to the skin of the patient. The base 8 also includes a retention section 8*d* which is the image shown in FIG. 10 is generally perpendicular to the tab 8*c*. The retention section 8*d* may be, for example, 2 to 5 inches wide and 6 to 16 inches long, thereby providing up to an additional 80 square inches of retaining portion of the base 8 for adhesively attaching to the patient's skin or another substrate. In one embodiment, the tab 8*c* is about 3 inches wide and 8 inches long and the retention section 8*d* is about 3.5 inches wide and about 12 inches long. Thus, the base 8 provides approximately 64 square inches of surface area, some or all of which can be used for disposing adhesive thereon to attach the base to the patient's skin or to a substrate.

Attached to the retention section 8*d* of the base 8 is a strap 12. The strap 12 may be attached to the base 8 by a variety of measures includes adhesives, rivets or other mechanical fasteners. As shown in FIG. 10, the strap 12 is attached to the base 8 by sewing the two together. The strap 12 may include a first end 12*a*, a central portion 12*c* and a second end 12*c*. In FIG. 10, the central portion 12*b* is sewn to the base. The first end 12*a* may include a fastener 12*d*, such as a buckle, a clip or hook and loop fastener. The second end 12*c* may include a corresponding second fastener 12*g* which engages the first fastener to secure the ends of the strap together. As shown in FIG. 10, the strap may be formed from nylon or a similar material.

Disposed on top of the strap 12 may be a wrist/ankle pad or other padded inner layer 12*f* forming a wrist pad which prevents the strap 12 from injuring the skin of the user and makes the device more comfortable. The wrist pad 12*f* may be formed from foam, neoprene or other known materials which are used for padding. In use, the base 12 is typically attached to the patient's skin or to an adjacent substrate depending on the limb being captured. The patient's wrist or ankle is placed on the wrist/ankle pad or padding 12*f* and then the first end 12*a* and the second end 12*c* are brought together, so that the strap surrounds the wrist or ankle. The fasteners 12*d* are attached and the limb may held in place as long as needed.

When the limb capture device is no longer needed, the limb may be released by disconnecting the fasteners 12*d* and the base may be pealed off the skin of the patient or the substrate. The limb capture device may then be discarded.

Figure 11:
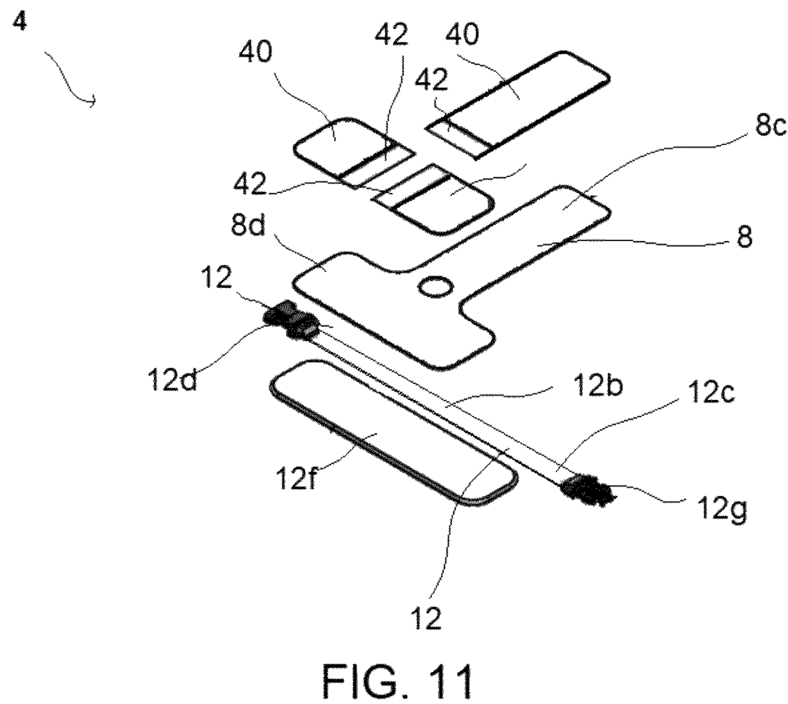
FIG. 11 shows an exploded view of the limb capture device of FIG. IO.

FIG. 11 shows an exploded bottom view of the various components of the limb capture device 4, which may include adhesive pads 40 which may be adhesively attached to the base 8 on one side, and may have plastic covers 42 on the other side for removal when the limb capture device is to be used. As shown in FIG. 11, three adhesive pads 40 are used, with one being disposed on the tab 8*c* and two being disposed on the retention section 8*d* of the base. It will be appreciated that a single adhesive pad or multiple pads may be used, and the pads could be attached to the base in multiple ways.

The other portions shown in FIG. 11 are numbered accordingly to those structures in FIG. 10 and the discussion therein applies to the limb capture device shown in FIG. 11.

It will further be appreciated that the use of the limp capture device 4 may be used somewhat differently depending on the procedure being done. In an IO procedure in the humoral head the base 8 will usually be attached to the patient's abdomen or at least to clothing on the patient. In contrast, if the limb capture device is being used to steady the arm of a person having Parkinson's while removing a mole or inserting an IV, the base 8 may be attached to a surface adjacent to the patient. Likewise, securing a patient's leg will typically involve the base being adhesively or otherwise mounted on a surface other than the patient's skin, such as an operating table, and examination table or an examination chair, etc.

Thus, there is disclosed a limb capture device. Numerous modifications to the various embodiments discussed herein will be apparent to a person of ordinary skill in the art and the appended claims are intended to cover such modifications.

What is claimed is:

1. A limb capture device comprising:

a base having an adhesive disposed thereon, wherein the base comprises a first section and a second section angled with respect to the first section, wherein the first section forms a retention section and is configured to secure a patient's limb within a loop formed by wrapping opposing ends of the first section around the patient's limb, and wherein the second section is longer than the first section and is configured to secure the limb capture device to the patient's skin;

a strap attached to the base, the strap being adjustable; and a guide configured to align the limb capture device with an anatomical marker comprising a navel of the patient, wherein the guide comprises an opening configured to provide visual alignment of the limb capture device relative to the anatomical marker during application such that visibility of the anatomical marker through the opening confirms proper placement of the limb capture device.

2. The limb capture device according to claim 1, further comprising a removable cover attached to the base so as to cover the adhesive.

3. The limb capture device according to claim 2, wherein the base has a bottom and wherein the adhesive is attached to the bottom.

4. The limb capture device according to claim 3, wherein the removable cover has a tab extending beyond the base.

5. The limb capture device according to claim 1, wherein the opening is formed adjacent to an intersection of the first section and the second section.

6. The limb capture device according to claim 5, wherein the opening is sized and configured to be positioned about the navel such that a wrist of the patient can be fixedly positioned adjacent to the navel after the limb capture device has been secured to the limb and to the patient's skin about the navel.

7. The limb capture device according to claim 1, wherein the base has a bottom surface, a portion of which has the adhesive disposed thereon and a portion of which lacks the adhesive thereon.

8. The limb capture device of claim 1, wherein the first and second sections of the base form an at least substantially T shape.

9. The limb capture device of claim 1, further comprising a cross-strap attached to the base for holding the strap to the base.

10. The limb capture device according to claim 1, wherein the first and second sections each comprises the adhesive configured to engage a patient's skin.

11. A limb capture device, comprising:

a base defining a shape at least substantially in a form of a letter T, at least a portion of the base being configured to form a loop to capture a patient's arm, the base having a bottom surface and adhesive disposed on the bottom surface, wherein the adhesive is configured to directly engage the patient's skin; and a strap attached to the base, the strap being generally on an opposing side of the base from the bottom surface and configured to wrap around the patient's arm; and a guide comprising an anatomical alignment opening formed in the base, the anatomical alignment opening configured to permit visual alignment relative to an anatomical marker comprising a navel of the patient during application by positioning the anatomical alignment opening about the anatomical marker such that visibility of the anatomical marker through the anatomical alignment opening confirms proper placement of the limb capture device.

12. The limb capture device according to claim 11, wherein the anatomical alignment opening comprises a navel alignment opening configured to allow a user to apply the limb capture device at a desired position and configuration with the patient's wrist being adjacent to the patient's navel and with the navel alignment opening positioned about the patient's navel.

13. The limb capture device according to claim 12, wherein the navel alignment opening is positioned adjacent to an intersection between a first section of the base and a second section of the base extending from the first section to form the letter T.

14. The limb capture device according to claim 11, further comprising a cover, wherein the cover is selectively removable from the base.

15. A method for securing a limb during a procedure, the method comprising, in either order:

a step of securing the limb of a patient in a limb capture device having a base and a strap attached to the base such that the strap holds the limb to the base, wherein the base comprises a first section and an arm extending from the first section, wherein the limb is secured in the limb capture device by wrapping the strap around the limb, the strap extending along and parallel to the first section;

a step of adhesively securing the base directly to the patient's skin to hold the limb adjacent to the patient's skin, wherein the arm is adhesively secured directly to the patient's skin along a side of the patient's abdomen, and wherein the first section and the arm are both adhesively secured directly to the patient's skin at angles relative to one another extending from the patient's navel;

aligning a navel guide with the patient's navel to provide visual confirmation of proper placement of the limb capture device, wherein the navel guide comprises an opening, and wherein the step of aligning the navel guide comprises placing the opening about the patient's navel.

16. The method according to claim 15, wherein the method comprises adhesively attaching the base to skin along the patient's abdomen so as to hold a lower portion of the patient's arm in a position extending across the patient's abdomen with a wrist of the patient positioned adjacent to the patient's navel.

17. The method according to claim 15, wherein the opening is positioned adjacent to an intersection between the first section and the arm.

18. The method according to claim 15, wherein the method comprises removing a cover attached to the base to expose a portion of the base having adhesive disposed thereon.

* * * * *